United States Patent [19]
Orndal et al.

[11] Patent Number: 4,797,655
[45] Date of Patent: Jan. 10, 1989

[54] DETECTOR SYSTEM FOR MONITORING A FLUID CONTAINING TUBE

[75] Inventors: Carl-Henry Orndal, Eslov; Bengt-Ake G. Gummesson, Bara; Bjorn-Inge Ericson, Lund, all of Sweden

[73] Assignee: Gambro AB, Sweden

[21] Appl. No.: 29,252

[22] Filed: Mar. 23, 1987

[30] Foreign Application Priority Data

Mar. 24, 1986 [SE] Sweden .............................. 8601354

[51] Int. Cl.[4] ............................................. G08B 19/00
[52] U.S. Cl. .................................... 340/521; 340/522; 340/619; 340/661; 340/686; 128/633; 250/336.1; 604/31; 604/67; 604/123
[58] Field of Search .............. 340/521, 522, 501, 500, 340/531, 870.28, 870.29, 612, 614, 615, 618, 619, 661, 603-606, 592, 686; 137/15.2, 38, 39, 100; 128/633, 634, 636, 645, 646, 664, 665, DIG. 3, 13; 604/31, 65, 66, 50, 67, 122, 123, 253, 256; 250/336.1, 338, 347, 491.1, 492.1, 493.1, 495.1

[56] References Cited

U.S. PATENT DOCUMENTS

| | | | |
|---|---|---|---|
| 4,080,967 | 3/1978 | O'Leary | 604/152 |
| 4,367,736 | 1/1983 | Gupton | 604/67 |
| 4,501,531 | 2/1985 | Bilstad et al. | 604/67 |
| 4,553,958 | 11/1985 | LeCocq | 604/67 |
| 4,681,563 | 7/1987 | Deckert et al. | 604/67 |

Primary Examiner—Donnie L. Crosland
Attorney, Agent, or Firm—Lerner, David, Littenberg, Krumholz & Mentlik

[57] ABSTRACT

Apparatus for monitoring fluid flow in dialysis systems include a tube holder for mounting the tube at a predetermined location on a dialysis monitor, a transmitter for transmitting a signal such as ultraviolet light through that location, a receiver for receiving the signal after it has passed through that location, and a sensor for sensing whether the tube is mounted at that location and whether the fluid is contained within the tube in response to the signal received by the receiver.

15 Claims, 2 Drawing Sheets

DETECTOR SYSTEM FOR MONITORING A FLUID CONTAINING TUBE

FIELD OF THE INVENTION

The present invention relates to detector systems for monitoring a fluid-containing tube. More particularly, the present invention relates to detector systems for monitoring fluid flow in a tube which can be connected to a monitor so as to control the flow within the tube. Still more particularly, the present invention relates to such detector systems which are intended to be applied to systems for the extracorporeal treatment of blood, such as dialysis. That is, in such systems the tubes are used for the flow of fluids which include either blood or a so-called priming fluid, i.e., a physiologically acceptable salt solution.

BACKGROUND OF THE INVENTION

Various systems have previously been devised for checking or monitoring fluid-carrying tubes assembled on monitors. For example, in dialysis monitors, air detectors are known for checking whether any air is accompanying the blood back to the patient. Furthermore, there are the so-called blood-leakage monitors which have been used in connection with dialysis monitors, which sound an alarm if they detect blood which has leaked over from the blood side to the dialysate. It is a disadvantage of these known systems, however, that they are directly adapted to the actual treatment involved. As a result, in certain cases they can create more problems than they resolve, such as during the so-called priming stage of a dialysis system. What has thus occurred is that during this priming step these types of blood leakage monitors tend to produce false alarms because of the presence of air bubbles during that priming phase. Thus, alarms are generated even though during this phase there clearly could not be any actual blood leakage. Furthermore, these air-flow monitors can naturally sound alarms during priming unless special measures are adapted to by-pass same.

It is therefore an object of the present invention to provide detector systems of the above-described type which are specifically adapted to facilitate the priming phase of such systems. More particularly, it is an object of the present invention to overcome all of the above-noted deficiencies in prior such detector systems.

SUMMARY OF THE INVENTION

In accordance with the present invention, these and other objects have now been achieved by providing apparatus for monitoring fluid flow systems which include a tube through which fluid is intended to flow and which comprises mounting means for mounting the tube at a predetermined location, transmitting means for transmitting a signal through that predetermined location, receiver means for receiving the signal after it has passed through that predetermined location, and sensing means for sensing whether the tube is mounted at the predetermined location and whether the fluid is contained within the tube in response to the signal received by the receiver means. In a preferred embodiment, the signal comprises infrared light.

In accordance with one embodiment of the apparatus of the present invention, the sensing means includes comparator means for comparing the signal received by the receiver means with a first predetermined reference signal to determine whether or not the tube is mounted at the predetermined location, and a second predetermined reference signal for determining whether or not the fluid is contained within the tube.

In accordance with a preferred embodiment of the apparatus of the present invention, the fluid comprises both first and second fluids, with the first fluid having a lower transmitting property for the signal than the second fluid, and in which the sensing means comprises dual sensing means for sensing whether the tube is mounted at the predetermined location and to determine whether either the first fluid or the second fluid is contained within the tube. Preferably, the first fluid is blood and the second fluid is a priming fluid. The sensing means preferably includes comparator means for comparing the signal received by the receiver means with a first predetermined reference signal to determine whether or not the tube is mounted at the predetermined location and with a second predetermined reference signal to determine whether or not the first fluid or the second fluid is contained within the tube. In a particularly preferred embodiment, the apparatus includes an alarm means for actuating some form of warning device, or for arming an alarm signal upon the sensing means sensing that the first fluid is contained within the tube.

In accordance with another embodiment of the apparatus of the present invention, the apparatus includes a monitor, and the mounting means, the transmitting means, and the receiving means are each mounted on the monitor. Preferably, the apparatus includes clamp means for clamping the tube to prevent the flow of fluid therethrough, and the clamping means is mounted on the monitor adjacent to the mounting means, so that the tube is automatically mounted on the clamping means when the tube is mounted at the predetermined location in the mounting means.

In accordance with a preferred embodiment of the apparatus of the present invention, pump means are provided for pumping the fluid through the tube, and the apparatus includes actuation means for deactivating the pump upon the sensing means sensing that the tube is not mounted at the predetermined location, for temporarily actuating the pump for a predetermined period of time upon the sensing means sensing that the tube is mounted at the predetermined location or that the second fluid is contained within the tube, and for actuating the pump upon the sensing means sensing that the first fluid is contained within the tube.

In accordance with another embodiment of the apparatus of the present invention, the transmitting means comprises conducting means for conducting the signal through the predetermined location in a direction outwardly or substantially perpendicularly away from the monitor, and in which the receiver means includes refractor means for refracting the signal back towards the monitor. Preferably, the mounting means comprises a generally circular passage for the tube, and includes securing means for securing the tube in that generally circular passage. In a preferred embodiment, the securing means comprises slot means for providing access to the generally circular passage, the slot means preferably having a width which is smaller than the width of the tube.

In accordance with another embodiment of the apparatus of the present invention, the transmitting means comprises means for transmitting the signal in a defined form, preferably a pulse train of a predetermined frequency. Most preferably, comparative means are provided for comparing the signal received by the receiver means with the signal in order to detect interference therein.

In accordance with another embodiment of the apparatus of the present invention, computer means are provided for providing the signal for transmission by the transmitting means, and secondary computer means are provided for providing first and second upper and lower reference signals, wherein the sensing means includes a first comparator for comparing the signal received by the receiving means with the upper reference signal, and a second comparator for comparing the signal received by the receiving means with the lower reference signal.

On an overall basis, the apparatus of the present invention includes a detector system which is able to sense on the one hand whether the tube is assembled in the correct position, and on the other hand whether it is filled or not. Thus, when this invention is applied to systems for the extracorporeal treatment of blood, such as dialysis, the tube can be filled with either blood or a priming fluid, and the receiver is joined to an arrangement to compare the values received with at least one reference value so that this comparison can be utilized in an arrangement which is programmed to establish:

(1) Whether the signal which is received exceeds a first higher reference value corresponding to the absence of a tube;

(2) Whether the signal which is received exceeds a second lower reference value which corresponds to the assembled tube, which is empty or filled with a substantially colorless fluid, such as a priming fluid; and (3) Whether the signal which is received falls short of the lower reference value, thus corresponding to the assembled tube being filled with blood.

Monitors of this type can also include one or more alarm functions which are intended to sound an alarm when critical limit values are exceeded or fail to be attained in such extracorporeal blood treatment procedures. One advantage of the present invention is that some of these alarm functions can be wholly disengaged or reduced in state (1) and/or (2), but can be brought into full operation as soon as state (3) above is reached.

Monitors which include the transmitters and receivers discussed above will normally have these and associated electrical components installed in the monitor itself or directly on the front face of the monitor. In that case the means for conducting the light beam can advantageously be included in a tube holder which is assembled on the front face of the monitor and through which the light is adapted to be conducted initially perpendicularly outward from the front face, and subsequently after it is passed through the tube it can be refracted in an opposite direction back towards the front face of the monitor. In this manner the risk of effects of external light interference are reduced while at the same time the holder has a rather simple overall design. For example, it can be formed in one piece of diecasting and provided with a circular passage or guide for the tube into which the tube can be inserted through a securing device, such as that in the form of a slot which is narrower than the tube itself.

BRIEF DESCRIPTION OF THE DRAWINGS

The present invention can be more fully appreciated with reference to the following detailed description, which refers to the attached drawings, in which.

DETAILED DESCRIPTION

Although this invention is preferably intended to be used for controlling dialysis systems, and will be described below with reference to such an application, it will be obvious to those versed in the art that this invention can also be applied, for example, to other extracorporeal blood treatment systems, and/or for the control, in general, of the flow of different fluids through a tube which can also be connected to such a monitor.

Figure 1:
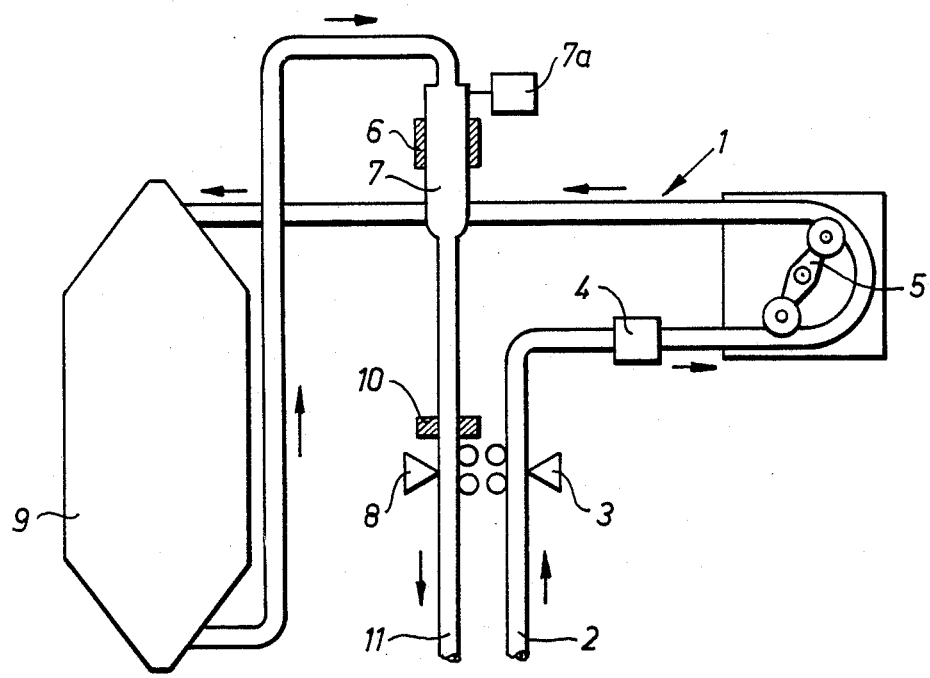
FIG. 1 is a schematic, partially sectional, representation of an overall system with which the detector system of the present invention is utilized.

Refering to the FIGURES, in which like numerals refer to like portions thereof, FIG. 1 thus shows such a tube or tube system which is intended to be used for the withdrawal of blood from a patient. The tube or tube system is normally connected to the front of a control monitor. For the sake of simplicity only certain of the primary components thereof are shown in FIG. 1. These include an arterial clamp, 3, which can be used to terminate the flow of blood therethrough, such as in connection with various alarms, an arterial pressure controller, 4, of a conventional type, a pump, 5, a combined air detector and holder, 6, for a drip chamber, 7, and a conventional venous clamp, 8. In FIG. 1 there is also shown a dialyzer, 9, and a detector, 10, which is an essential component of the present invention. The detector, 10, is in this case arranged directly connected to the venous clamp, 8, in a manner such that the tube can be assembled in the detector only when it is also assembled in the venous clamp, 8. Reference numeral 11 designates the outlet end of the tube or tube set, 1, which in this case is intended to be connected to the patient for return of the blood after dialysis. Finally, reference numeral 7a in FIG. 1 designates a venous pressure gauge connected to the drip chamber, 7. The arterial pressure controller, 4, and the venous pressure gauge, 7a, are appropriately connected to different pressure gauges, and to a computer included in the monitor, in a manner such that an alarm is activated when certain pressure limits are either exceeded or fail to be reached.

Figure 2:
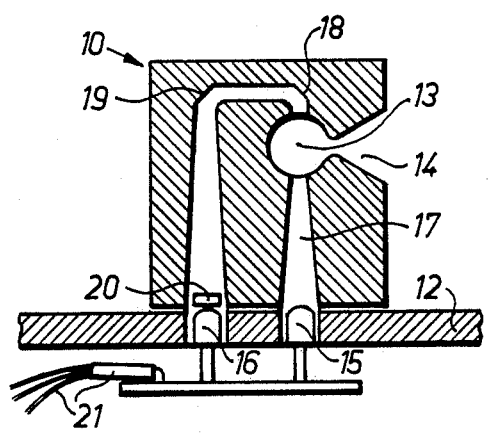
FIG. 2 is a side, elevational, partially sectional view of a detector in accordance with the present invention.

Referring next to FIG. 2, there is shown the detector, 10, fitted onto the front face of a monitor, 12. The actual tube holder is formed by a circular passage or guide 13, into which the tube can be inserted through a securing device, 14, which in this case is in the form of a slot which is preferably narrower than the width of the tube. Within the front face of the monitor is a transmitter, 15, preferably for infrared light, which is assembled in conjunction with a receiver, 16, for the same light. The light is thus passed through a light conductor, 17, through the circular passage, 13, and thereby through the tube, 1, if the tube is in the appropriate location. The light is then refracted by means of angled surfaces, 18 and 19, so that, after passing through a wavelength filter, 20, it is directed towards receiver, 16. Reference numeral 21 finally designates means by which the transmitter and the receiver can be connected to the rest of the electronics within the monitor. This electronics pack is described in more detail in connection with FIG. 3.

Figure 3:
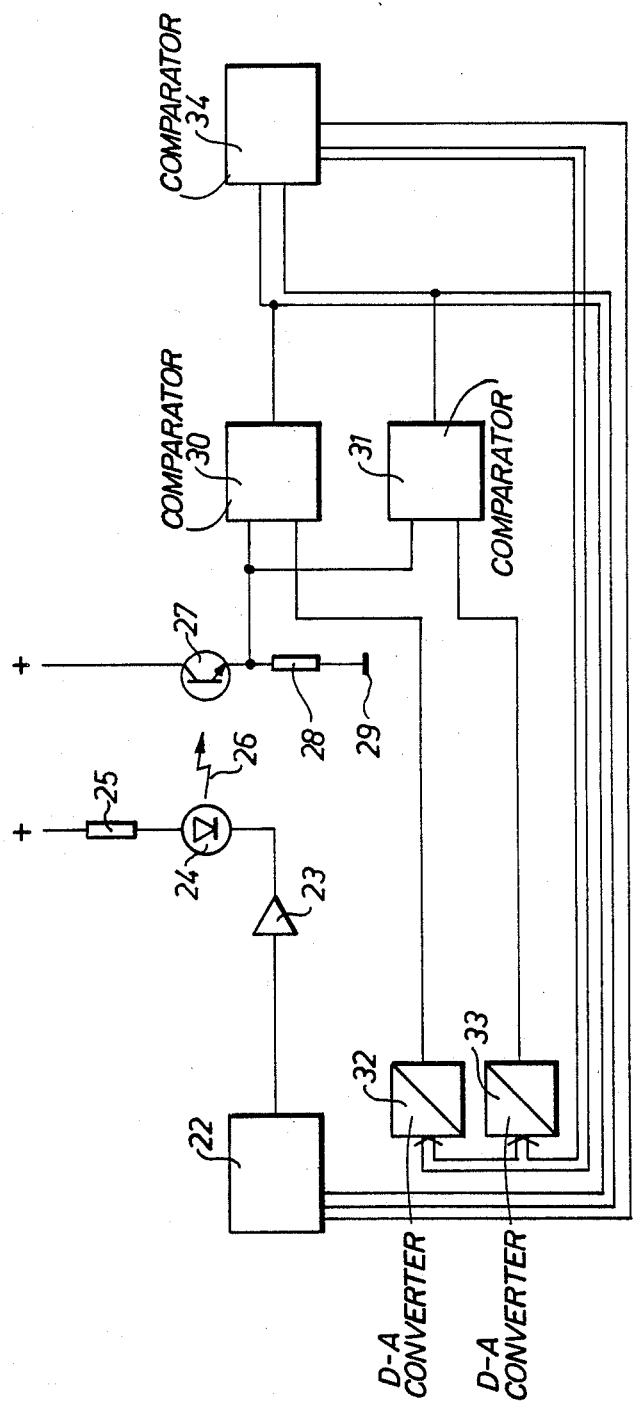
FIG. 3 is a schematic, circuit diagram of the detector system of the present invention.

Referring next to FIG. 3, this electronics pack may, of course, be designed in many different ways. In a preferred design, as shown in FIG. 3, a main computer 22 is adapted to put out a signal by means of a driver stage, e.g., a transistor, 23, to an infrared light-emitting diode, 24, which is connected to a positive pole through a resistor, 25. From the light-emitting diode, 24, a light beam, 26, is emitted, which is received by a phototransistor, 27, which on one side is connected to a positive pole and on the other side, through a resistor, 28, to ground 29. The signal which is thus obtained is passed to two comparators, 30 and 31, each of which receives a reference signal from a so-called safety computer, 34, by means of two converters, 32 and 33. The latter two converters convert a digital signal from the safety computer, 34, to an analogue signal, which can be compared with the analogue signal from the phototransistor, 27. The upper converter, 32, transmits a higher reference signal corresponding to a wholly disconnected tube, whereas the lower converter, 33, transmits a lower signal corresponding to a properly located empty tube, or such a tube filled with a substantially transparent fluid. By means of the comparators, 30 and 31, it is thus possible to establish whether a tube is installed in the holder, 10, at all, and whether or not this tube is filled with blood. If blood is present in the tube, the signal, 26, is practically wholly extinguished, so that the value obtained from the phototransistor, 27, will be clearly located below the reference signal from the converter, 33. Values obtained from the comparators, 30 and 31, are transmitted not only to the main computer, 22, but also to the above-mentioned auxiliary or safety computer, 34.

The plastics from which the above-mentioned tubes are normally manufactured have essentially no absorption peaks within the range of from about 850 nm to 1000 nm. Therefore, the wavelength of the infrared light is appropriately selected from within this range. It has thus been found to be particularly suitable to use a wavelength of about 940 nm where these plastic materials have practically no absorption at all. The refractive index of these plastics is normally within the range of from about 1.4 to 1.6, depending on the material selected and the wavelength of the light utilized. They may be utilized to detect an empty tube or a tube filled with a substantially transparent fluid. In view of the fact that these tubes are round, they act as a lens, and refract the light. This causes the intensity of the light to diminish on the receiving side. In order to thus obtain the same measured value every time under the same conditions, the tube must not be deformed in the holder, but should be "loose" within the holder, while at the same time it must still be maintained in the desired location.

It is also helpful to calibrate the detector before any tube is inserted within the holder. The purpose of doing as is to compensate for any ripples within the light transmission system. If a tube is already incorporated in the holder, 10, when the system is put into operation, then the computer, 22, may be adapted so that it is activated from the results of the last such calibration.

The smallest opening within the light conductor, 17, on the transmitter side shall preferably be selected on the basis of the smallest dimension of the tube which is intended to be used therein. In practice, it has thus been found appropriate to use a circular opening of a diameter of about 1.5 mm, a square opening of about 1.5 mm side length, or a gap of about 1.5 mm×5 mm. The corresponding smallest opening on the receiver side ought to be slightly larger. For example, it may have a corresponding diameter or side of about 2 mm. In this manner, good reliability can be obtained with different tube diameters, down to at least about 1.5 mm. Such fine-caliber tubes, however, should be fixed in the light beam path in some way.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. Apparatus for monitoring a fluid flow system including a tube through which fluid is intended to flow comprising mounting means for mounting said tube at a predetermined location, transmitting means for transmitting a signal through said predetermined location, receiver means for receiving said signal after it has passed through said predetermined location, and sensing means comprising comparator means for comparing said signal received by said receiver means with a first predetermined reference signal for determining whether or not said tube is mounted at said predetermined location and with a second predetermined reference signal for determining whether or not said fluid is contained within said tube, whereby both said determinations can be made on the basis of the same signal received by said receiver means.

2. The apparatus of claim 1 wherein said signal comprises infrared light.

3. The apparatus of claim 1 wherein said fluid comprises first and second fluids, said first fluid having a lower transmitting property for said signal than said second fluid, and wherein said comparator means comprises dual comparator means for sensing whether said tube is mounted at said predetermined location and for determining whether either said first fluid or said second fluid is contained within said tube.

4. The apparatus of claim 3 wherein said first fluid comprises blood and said second fluid comprises a priming fluid, and wherein said comparator means comprises means for comparing said signal received by said receiver means with a first predetermined reference signal for determining whether or not said tube is mounted at said predetermined location and with a second predetermined reference signal for determining whether or not said first fluid or said second fluid is contained within said tube.

5. The apparatus of claim 4 including alarm means for actuating an alarm upon said sensing means sensing that said first fluid is contained within said tube.

6. The apparatus of claim 1 including a monitor, and wherein said mounting means, said transmitting means, and said receiving means are mounted on said monitor.

7. The apparatus of claim 6 including clamp means for clamping said tube so as to prevent said flow of said fluid therethrough, said clamping means being mounted on said monitor adjacent to said mounting means whereby said tube is automatically mounted on said clamping means when said tube is mounted at said predetermined location in said mounting means.

8. The apparatus of claim 4 including pump means for pumping said fluid through said tube, and actuation means for deactivating said pump upon said sensing means sensing that said tube is not mounted at said predetermined location, for temporarily actuating said pump for a predetermined period upon said sensing means sensing that said tube is mounted at said predetermined location or that said second fluid is contained within said tube, and for actuating said pump upon said sensing means sensing that said first fluid is contained within said tube.

9. The apparatus of claim 6 wherein said transmitting means comprises conducting means for conducting said signal through said predetermined location in a direction outwardly from said monitor, and wherein said receiver means includes refractor means for refracting said signal back towards said monitor.

10. The apparatus of claim 9 wherein said mounting means comprises a generally circular passage for said tube, and including securing means for securing said tube in said generally circular passage.

11. The apparatus of claim 10 wherein said securing means comprises slot means for providing access to said generally circular passage, said slot means having a width smaller than the width of said tube.

12. The apparatus of claim 1 wherein said transmitting means comprises means for transmitting said signal in a defined form.

13. The apparatus of claim 12 wherein said defined form comprises a pulse train of a predetermined frequency.

14. The apparatus of claim 13 including comparative means for comparing said signal received by said receiver means with said signal in order to detect interference therein.

15. The apparatus of claim 1 including computer means for providing said signal for transmission by said transmitting means, and secondary computer means for providing said first and second predetermined reference signals.

* * * * *